United States Patent
Hasling

(10) Patent No.: US 9,233,147 B1
(45) Date of Patent: Jan. 12, 2016

(54) NANO-VECTOR PRODRUG DELIVERY SYSTEM

(75) Inventor: Thomas Alan Hasling, Honolulu, HI (US)

(73) Assignee: Oceanit Laboratories, Inc., Honolulu, HI (US)

( * ) Notice: Subject to any disclaimer, the term of this patent is extended or adjusted under 35 U.S.C. 154(b) by 700 days.

(21) Appl. No.: 12/799,094

(22) Filed: Apr. 16, 2010

Related U.S. Application Data

(60) Provisional application No. 61/212,959, filed on Apr. 17, 2009.

(51) Int. Cl.
| | |
|---|---|
| *A61K 48/00* | (2006.01) |
| *C12N 15/86* | (2006.01) |
| *C12N 15/00* | (2006.01) |
| *A61K 39/00* | (2006.01) |
| *B82Y 5/00* | (2011.01) |

(52) U.S. Cl.
CPC . *A61K 39/00* (2013.01); *B82Y 5/00* (2013.01); *A61K 2039/5258* (2013.01); *C12N 15/00* (2013.01)

(58) Field of Classification Search
CPC .............................. B82Y 5/00; C07K 16/2809
USPC ........... 424/184.1, 193.1, 400, 489, 490, 499; 435/456; 514/1.2; 977/742
See application file for complete search history.

(56) References Cited

U.S. PATENT DOCUMENTS

| | | | | |
|---|---|---|---|---|
| 2006/0275371 | A1* | 12/2006 | Dai et al. ....................... | 424/489 |
| 2008/0003293 | A1* | 1/2008 | Hirsch et al. ................... | 424/489 |

OTHER PUBLICATIONS

Pantarotto et al. Chemistry & Biology, vol. 10, 961-966, Oct. 2003.*
Bar et al. BMC Biotechnology 2008, 8:37, pp. 1-14.*
Duncan, Ruth, "Polymer Conjugates as Anticancer Nanomedicines", Nature.com/Reviews/Cancer, Sep. 2006, vol. 6, pp. 688-701.
Iyer et al., "Exploiting the Enhanced Permeability and Retention Effect for Tumor Targeting", Drug Discovery Today, vol. 11, Nos. 17/18, Sep. 2006, pp. 812-818.
Kam et al., Carbon Nanotubes as Multifunctional Biological transporters and Near-Infrared Agents for Selective Cancer Cell Destruction, Poc. Natl. Acad. Sci, Aug. 2005, vol. 102, No. 33, pp. 11600-110605.
Medina et al., Targeted Liposomal Drug Delivery in Cancer, Current Pharmaceutical Design, 2004, vol. 10, No. 24, pp. 2981-2989.
Muro et al., "Endothelial Targeting of High-Affinity Multivalent Polymer Nanocarriers Directed to Intercellular Adhesion Molecule 1", Journal of Pharmacology & Experimental Therapeutics, 2006, vol. 317, No. 3, pp. 1161-1169.
Yacoby et al., "Targeted Drug-Carrying Bacteriophages as Antibacterial Nanomedicines", Antimicrobial Agents & Chemotherapy, 2007, vol. 51, No. 6, pp. 2156-2163.
Dreaden et al., "Tamoxifen-Poly(ethylene glycol)-Thiol Gold Nanoparticle Conjugates", Bioconjug Chem., Dec. 2009, pp. 1-15.
Yavuz et al., "Gold Nanocages Covered by Smart Polymers for Controlled Release with Near-Infrared Light", Nat Mater., Dec. 2009, pp. 1-10.
Welsher et al., "A Route to Brightly Fluorescent Carbon Nanotubes for Near-Infrared Imaging in Mice", Nat Nanotechnol. Nov. 2009, pp. 1-15.
Loo et al., "Immunotargeted Nanoshells for Integrated Cancer Imaging and Therapy", Nano Letters, 2005, vol. 5, No. 4, pp. 709-711.

\* cited by examiner

*Primary Examiner* — Janet Epps-Smith
(74) *Attorney, Agent, or Firm* — James Creighton Wray; Meera P. Narasimhan

(57) ABSTRACT

A first set of carbon nanotubes is functionalized with streptavidin and co-functionalized with a cell treatment payload material. A second set of carbon nanotubes is functionalized with biotin and co-functionalized with specific cell targeting material. Mixing the first and second sets causes four carbon nanotubes from the second set to attach to each carbon nanotube from the first set. Multiple replicated virus-like particles result. The pharmaceutical composition seeks out and attaches to target cells. The carbon nanotubes from the first set penetrate the targeted cells and deliver their cell treatment payloads into the targeted cells. Near infrared energy is transmitted through tissue heating the carbon nanotubes for targeted cell treatment.

32 Claims, 3 Drawing Sheets

NANO-VECTOR PRODRUG DELIVERY SYSTEM

This application claims the benefit of U.S. Provisional Application No. 61/212,959, filed Apr. 17, 2009, which is hereby incorporated by reference in its entirety.

SUMMARY OF THE INVENTION

Prodrug-based drug delivery systems have the promise to augment the efficacy of compounds with limited bioavailability to solid tumors. The invention provides a unique approach for a targeted prodrug delivery system. The system has the potential to deliver other therapeutic agents as well. This novel approach may be used toward enhancing the efficacy of therapeutic agents for breast and prostate cancer. The ultimate goal is to provide increased bioavailability at the tumor site and decreased toxicity to the patient.

Applications of the proposed technology are considerable for DoD, other government organizations and commercial utilization. The commercial potential of this invention is high. Drug delivery vehicles that demonstrate effectiveness in reducing tumor sizes or recurrence have widespread application for the treatment of cancer patients with solid tumors in both military and civilian sectors. The agents of this invention may be used as vehicles for any number of drugs to boost their efficacies. Additional benefits may include improving the diagnostic accuracy of medical imaging. According to a newly released report, nanotechnology-enabled drug delivery systems will generate over $1.7 billion (US) in 2009 and over $4.8 billion in 2012. The global drug delivery products and services market is projected to surpass US $67 billion in 2009.

Keywords concerning the invention are drug delivery, immunoconjugates, cell targeting, chemotherapy, cancer therapy.

The new Nano-Vector Prodrug Delivery System provides the ability to construct a highly targeted delivery platform and deliver a variety of compounds. Additionally the Nano-Vector can be triggered non-invasively to release the payload or rupture the targeted cell.

Systemic administration of chemotherapeutic agents, in addition to the anti-tumor benefits, results in indiscriminate drug distribution and severe toxicity. Prodrug strategies have been employed in attempts to address these issues. Prodrugs have the advantage that they are administered in an inactive form and then are metabolically or chemically activated in the tissues. Although that strategy reduces the generalized distribution of the active drug, it is certainly not specific, and much of the drug is activated in healthy tissues, which contributes to toxicity and limits bioavailability of the drug at the tumor site. These shortcomings may be overcome by target specific drug-carrying platforms that ferry the drug to the tumor site, while limiting exposure to non-target tissues and organs. A need exists for a reliable, flexible platform that specifically targets cancer cells and results in intracellular drug release and activation. Such a platform potentiates existing prodrugs by several orders of magnitude by increasing the bioavailability of the drug at the specific site. Additionally, this new platform reduces the overall required dose and the attendant toxicity to the patient.

Since the introduction of monoclonal antibodies (mAbs), and the initial clinical trials of antibody therapy in cancer patients, there has been progress in antibody based therapeutics, particularly in oncology. The usage of naked monoclonal antibodies has gradually evolved into drug immunoconjugates. In general, drug immunoconjugates are composed of targeting entities (mainly mAbs) chemically conjugated to a cytotoxic drug. The outcome is improved drug efficacy with reduced systemic toxicity. To date, the most clinically-advanced forms of armed antibodies are antibody-isotope and antibody-drug conjugates. Key issues in creating and testing potential agents for targeted therapy include the nature of the target molecule, its abundance at the target, and its specificity for the target, and the linkers used to attach the drug to the targeting moiety. As the advantages of targeted therapy have become more apparent, additional targeting moieties that are not antibody based, such as short peptides, non-antibody ligand-binding proteins, and even non-proteinaceous molecules such as carbohydrates are receiving increased attention.

Another class of targeted drug delivery platforms are the drug-carrying nanomedicines, such as liposomes, nanoparticles, drug-loaded polymers and dendrimers. With a few exceptions such as targeted liposomes, and antibody-targeted polymeric carriers, nanomedicines do not utilize a targeting moiety to gain target specificity. Rather, they rely on the enhanced permeability and retention (EPR) effect that results from the rapid deployment of blood vessels within rapidly growing tumors, resulting in blood vessels in the tumor being irregular in shape, dilated, leaky or defective. As a result, large drug carrying platforms may gain selective access to the tumor, while their exit from the bloodstream at non-target sites is limited. While the immunoconjugates are limited in drug-carrying capacity, usually less than 10 drug molecules per targeting moiety, nanomedicines by nature deliver a much larger payload to the target cells. Recently, bacterial phages were exploited for targeted delivery by applying them as anti-bacterial nanomedicines. The targeted phages were chemically conjugated, via a cleavable bond to a large payload of an antibiotic, with a maximal loading capacity of more than 10,000 drug molecules/phage (Yacoby, Bar et al. 2007). The anti-bacterial system was based on drug release at (and not within) the target site.

Delivering molecules and compounds into biological cells has proven to be a daunting obstacle to overcome for researchers and pharmaceutical companies. Intracellular delivery is difficult, because the cell membrane is specifically designed to keep the outside and inside of the cell chemically and electrically isolated. A variety of techniques have been used to 'trick' cells into accepting the molecules. Biologically inspired transport vehicles such as transferin, lipid vacuoles, and vitamins A and C are commonly used. Synthetic structures such as gold colloid and carbon nanotubes have also been used. Other methods include the transient disruption of the cell membrane using an electrical arc or chemically weakening the membrane. Although these techniques have been shown to deliver molecules into the cell, they lack cellular specificity. The majority of existing techniques will deliver the molecules into any and all cells. This is particularly undesirable in whole organism and therapeutic applications.

The new Nano-Vector Drug Delivery System is inspired by biological viruses and provides a revolutionary concept for delivering drugs to specifically targeted cells. A virus/phage is a relatively simple but yet ingeniously elegant structure. It is for all practical purposes a self assembling, self replicating nano-machine. Viruses can be highly specific to species and cell type. A bacterial phage 10 is constructed of the capsid 12, rod 14, and tails 16. (See FIG. 2). Upon contacting the host cell, the tails recognize membrane molecules and trigger the rod and capsid to lower to the cell membrane. The rod impales the cell membrane, and the phage injects its genomic material into the host cell.

The invention creates and constructs a synthetic analog of biological viruses. Using biological molecules and synthetic materials such as carbon nanotubes (CNTs), self assembling structures that resemble and mimic the behavior of biological viruses are created. The Nano-Vector targets specific cells, penetrates the cell membranes, and delivers molecules or compounds of choice. This is of particular relevance to the treatment of solid tumor cancers such as prostate and breast cancer.

Carbon nanotubes (CNTs) are quasi-one-dimensional, nearly single crystalline (axially), hollow, graphitic carbon structures. (See FIG. 1). The topology of nanotubes leads to extremely high thermal conductivity in the axial direction. Single-walled nanotubes can be either semiconducting or metallic, and their electrical properties can be tailored by tube diameter and helicity. The combination of high aspect ratio, small size, high strength, high stiffness, low density, and high thermal and electrical conductivity make them perfect candidates as backbones for nanostructures. CNTs are ideal structural components for the Nano-Vector with the following characteristics:

- highly hydrophobic and easily penetrate the cellular membranes
- easily functionalized with molecules of choice
- small (~1.4 nm diameter) but structurally rigid
- readily fabricated
- chemically/biologically inert These and further and other objects and features of the invention are apparent in the disclosure, which includes the above and ongoing written specification, with the claims and the drawings.

DETAILED DESCRIPTION OF THE DRAWINGS

Figure 1:
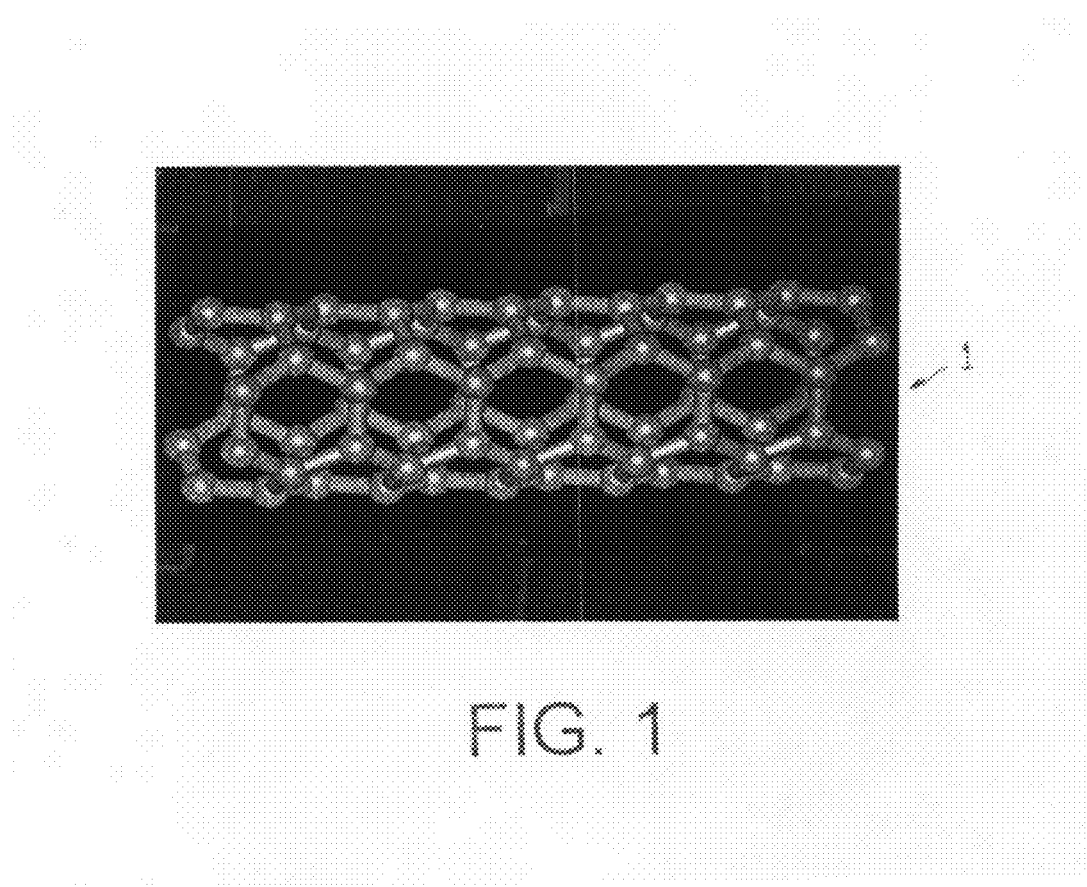
FIG. 1 is a computer model of a single wall CNT made up entirely of carbon atoms.

FIG. 1 is computer modeled ball and stick diagram of a single walled CNT 1. CNTs are made up entirely of carbon atoms in the form of a hollow tube. This arrangement of carbon atoms makes CNTs extremely strong, rigid, and thermally/electrically conductive. While the side walls are made up of entirely hexagonal rings, the end caps (not shown) have occasional pentagonal rings in order to form a half sphere (much like the stitching of a soccer ball). The pentagonal rings make the end caps chemically susceptible and allow functionalization with secondary molecules.

A variety of biological molecules/structures are used to assemble the Nano-Vector, target specific cells, and deliver the payload.

Figure 2A:
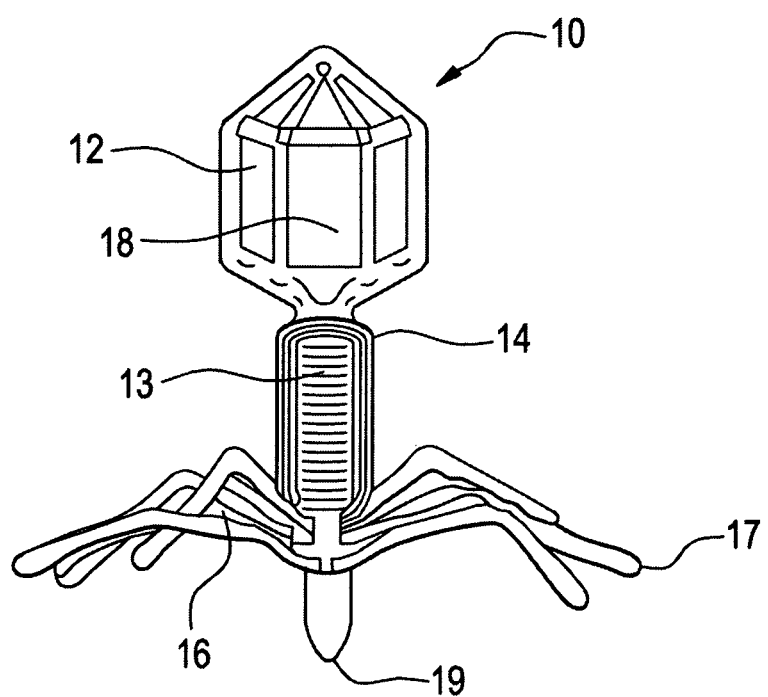
FIG. 2a is a depiction representative of a biological virus.

The virus 10 depicted in FIG. 2a is representative of a biological virus. The viral DNA/RNA 18 is contained in the capsid 12. A sheath 13 is attached to a rod 14. The tails 16 attached to the rod 14 have cell recognition molecules on the tips 17. Upon binding to the target cell, the end 19 of the rod penetrates the cell wall, and the nucleic acid sequences 18 are injected into the cell.

Figure 2B:
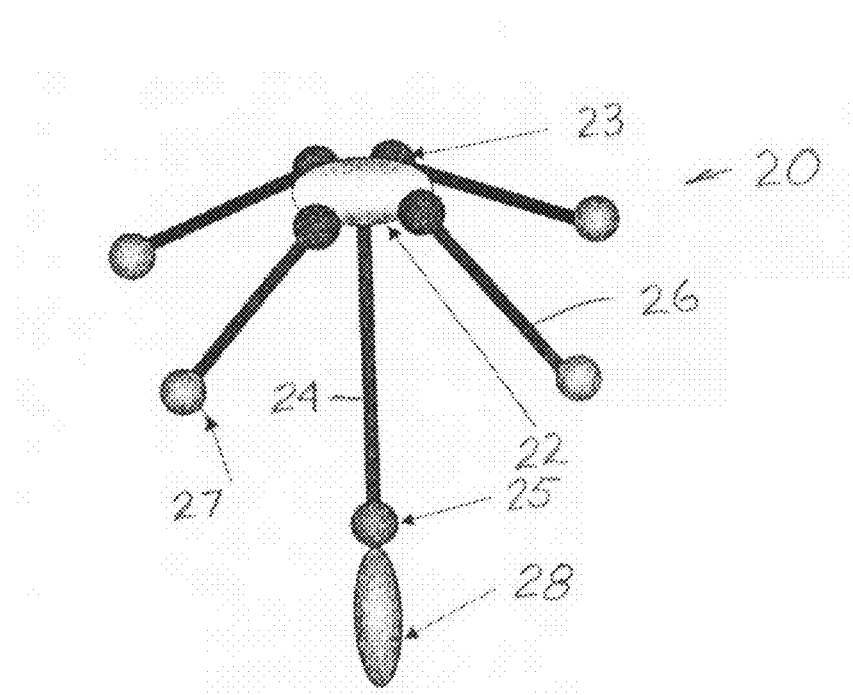
FIG. 2b is a schematic representation of a Nano-Vector.

The conceptual Nano-Vector depicted in FIG. 2b is constructed with CNTs functionalized with a variety of molecules.

Streptavidin and biotin are the self-assembling structural molecules. Streptavidin is a tetrameric protein purified from the bacterium *Streptomyces avidinii*. It has wide use in molecular biology through its extraordinarily strong affinity for the vitamin biotin. The dissociation constant (Kd) of the biotin-streptavidin complex is on the order of ~10-15 mol/L, ranking among one of the strongest known non-covalent interactions. One streptavidin molecule binds four biotin molecules. Tips of CNTs 24 are functionalized with streptavidin 22, which will represent the viral rod 14 in FIG. 21. Another set of CNTs 26 functionalized a first ends with biotin represents the viral tails 16 shown in FIG. 21. When these functionalized CNTs are combined, they will self assemble into a stable, viral-like structures 20—a single rod 24 with four tails 26

The primary structure of the Nano-Vector 20 is centered around the streptavidin core 22. The tails 26 self assemble to the body 20 when the biotin 23 irreversibly binds to the streptavidin 22. Each tail 26 is co-functionalized with a targeting molecule 27 that will specifically bind to a specific cell membrane protein. The rod analog 24 of the Nano-Vector 20 is co-functionalized with a linker molecule 25 or payload molecules 28 that release into the cytoplasm of the target cell.

The tails 26 of the Nano-Vector are co-functionalized with appropriate targeting molecules 27. The tails 26 are functionalized with m antibodies (mAbs) 27 that are specific to the targeted cells. This creates four target binding sites 27 per Nano-Vector 20. The multiple recognition sites increase the specificity of the Nano-Vector 20 and create a stabilized platform for the payload 28 to be delivered. The targeting molecules 27 can be substituted with alternate molecules to increase specificity, binding affinity, or target selection. Possible targeting molecules include short peptides, non-antibody ligand-binding proteins, or even synthetic ligand-binding molecules. The targeting molecules could all be the same or a combination of various molecules.

The rod 24 of the Nano-Vector 20 is co-functionalized with the payload molecules 28. The payload molecules 28 can be functionalized directly to the rod CNT 24 or contained in a secondary delivery structure such as a liposome or microsphere. Thousands of prodrug molecules can be loaded into a liposome that is then attached to the rod CNT 24. Naked CNTs are highly hydrophobic and easily penetrate cell membranes to deliver the payload molecule. Alternatively, the secondary delivery structure is designed to fuse with the target cell and release the payload molecules 28 into the cytoplasm by using molecules such as transferin or vitamin C.

Nano-Vector 20 could also be used to deliver drugs to the immediate extracellular domain or potentially directly disrupt the targeted cell. Single wall CNTs have been shown to absorb near infrared light (700-1100 nm) preferentially as compared with the surrounding biological structures. The specific heating of the CNTs has been used to disrupt an associated liposomes or induce proximal cell death. Since biological tissues are nearly transparent to near-infrared light, external illumination can be used to activate the targeted Nano-Vector 20 specifically at the illuminated tumor site. This property is particularly applicable to solid tumor cancers, such as breast cancer and prostate cancer. Specific release of the payload at the tumor site will decrease toxicity and increases bioavailability of the drug.

The Nano-Vector 20 is created to combine and leverage several existing cancer therapy strategies:

EPR—enhanced permeability and retention—The leaky nature of tumor vasculature will enhance the retention of the Nano-Vector at the tumor site.

Specificity—Nano-Vector 20 has multiple targeting molecules 27 and can use combinations of targeting molecules to be highly specific. This has the advantage of increased drug bioavailability at the tumor site and decreased systemic toxicity.

Intracellular delivery—Taking advantage of the hydrophobic nature of CNTs and the ability to functionalize CNTs, the Nano-Vector can release the payload inside of the targeted cell. This advantage increases efficacy and decreases toxicity.

Large payload—The Nano-Vector can be created to carry large payloads of the therapeutic agent—several thousand copies. Additionally, the Nano-Vector could carry multiple types of therapeutic agents (e.g. cocktails of prodrugs, chemotherapy drugs, and radio isotopes).

Prodrugs—The advantages of prodrugs will be greatly enhanced by the increased specificity and bioavailability provided by the Nano-Vector.

Builds on targeted bacterial phage research—Nano-Vector builds on a body of research using modified phages as drug delivery platforms, however, the Nano-Vector has the advantage of being entirely customizable and more stable.

Modular—The modular nature of the Nano-Vector may be applied to a wide range of applications in biology and medicine.

The Nano-Vector can be applied to other applications in biology and medicine. Some of these applications include:

Intracellular drug delivery: Several new classes of drugs are specifically targeting subcellular targets, rather than affecting the tissues or organs on a macro level.

Stem Cell Research and Therapy: Stem cells inevitably will be a major component in the treatment of disease and pathology. A major objective for stem cell research is to harvest or create adult stem cells from the eventual recipient. The introduction of transcription factors into epidermal cells and bone marrow cells that convert them to pluripotent stem cells is showing tremendous promise. The technology provides an effective method to introduce these transcription factors.

Genetic Engineering/Therapies: Mutated or abnormal DNA is the root cause of a myriad of pathologies. The technology could be a significant advance toward delivering DNA to targeted cells.

Antimicrobial: Nano-Vector could be used to target bacteria and release large doses of antibiotics (or cocktails of antibiotics) directly at the bacteria. This will increase the efficacy of the antibiotics and reduce undesirable side-effects to the patient.

The self assembling, targeted, drug carrying platform resembles and mimics biological viruses. The Nano-Vector platform is a nano-composite of CNTs, biological molecules, and payload drugs. Parameters are optimized for the self assembly and target specific delivery of the payload drug with the anticipation of in vivo animal trials in phase II.

Nano-Vector Platforms:
Co-functionalize single wall CNTs (SWCNTs) with multiple biological molecules,
Target co-functionalized SWCNTs to specific cells or targets,
Induce self assembly of a predetermined viral-like structure, and
Target the viral-like structures to specific cells or targets.

To co-functionalize SWCNTs with multiple biological molecules, protocols functionalize the opposite ends of the CNTs with different selected biological molecules.

While the invention has been described with reference to specific embodiments, modification and variations of the invention may be constructed without departing from the scope of the invention, which is defined in the following claims.

I claim:

1. Drug delivery Nano-Vector apparatus (20) comprising a core (22),
plural carbon nanotube tails (26) having first and second ends and functionalized at the first ends with self-assembling materials (23) irreversibly bound to the core (22) and co-functionalized at the second ends with targeting molecules (27) for specific cells, the targeting molecules (27) adapted to recognize and bind to specific cell membrane molecules, and
at least one nano rod (24) made of at least one other carbon nanotube functionalized at the first end with self-assembling materials as the core or irreversibly bound to the core (22), the at least one nano rod is co-functionalized (25) at the second end with payload treatment molecules (28) for the specific cell membrane molecules to which the targeting molecules bind, wherein said drug delivery Nano-Vector apparatus has a structure as set forth in FIG. 2b.

2. The apparatus of claim 1, wherein the core comprises a first set of the carbon nanotubes functionalized with a first affinity agent, and the tail nanomaterials comprise a second set of the carbon nanotubes functionalized with a second complementary affinity agent having an affinity for the first agent.

3. The apparatus of claim 2, wherein the first affinity agent and the second complementary affinity agent are biological molecules.

4. The apparatus of claim 1, wherein the first affinity agent is a tetra metric protein.

5. The apparatus of claim 4, wherein the tetra metric protein is a streptavidin.

6. The apparatus of claim 5, wherein the second affinity agent is biotin.

7. The apparatus of claim 2, wherein the first and second affinity agents are respectively streptavidin and biotin for self assembling the plural nanotubes into plural virus-like assemblies.

8. The apparatus of claim 7, wherein first ends of the plural biotin co-functionalized carbon nanotubes of the second set are attached to streptavidin functionalized carbon nanotubes of the first set.

9. The apparatus of claim 7, wherein the first set of streptavidin co-functionalized carbon nanotubes are co-functionalized with the payload cell treatment molecules for the specific cells.

10. The apparatus of claim 9, wherein the biotin-functionalized carbon nanotubes of the second set are co-functionalized with the specific cell targeting material.

11. The apparatus of claim 10, wherein plural biotin co-functionalized carbon nanotubes of the second set are attached to each streptavidin co-functionalized carbon nanotubes of the first set.

12. The apparatus of claim 2, wherein the first and second affinity agents are respectively for self assembling the plural differentially co-functionalized nanotubes into plural virus-like assemblies.

13. The apparatus of claim 8, wherein plural co-functionalized carbon nanotubes of the second set are attached to each co-functionalized carbon nanotubes of the first set.

14. The apparatus of claim 10, wherein the first set of co-functionalized carbon nanotubes are co-functionalized with the payload cell treatment molecules for the specific cells.

15. The apparatus of claim 1, wherein the materials co-functionalized with the specific cell targeting molecules have combinations of cell targeting molecules.

16. The apparatus of claim 2, wherein the carbon nanotubes co-functionalized with the treatment molecules penetrate cell walls to which the carbon nanotubes co-functionalized with the cell targeting molecules are attached.

17. The apparatus of claim 1, wherein the plural nanomaterials and the self-assembling materials further comprise a first nanomaterial structure functionalized with a first binding agent and co-functionalized with cell treatment molecules, a second set of plural nanomaterial structures functionalized with a cooperating complementary binding agent and co-functionalized with the specific cell targeting molecules, the second set of nanomaterial structures being attached to the first nanomaterial structure by the first binding agent and the cooperating complementary binding agent.

18. The apparatus of claim 17, wherein the nanomaterial structures are carbon nanotubes.

19. Cell targeting Nano-Vector apparatus comprising a core, the core further comprising a first set of carbon nanotubes functionalized with a first affinity agent, a second set of carbon nanotube tails having first ends functionalized with specific cell targeting molecules and having second ends functionalized with a second affinity irreversibly bound to the core and at least one drug delivery nano rod having a second end having a first end bound to the core and having a second end carrying a targeted cell treatment drug for treating cells with cell membrane molecules to which the targeting molecules bind, wherein the drug delivery Nano-Vector apparatus has a structure are set forth in FIG. 2b.

20. A drug delivery process comprising
functionalizing a core having a first set of plural nanomaterials with a first affinity agent, co-functionalizing first ends of a second set of carbon nanotubes with a second affinity agent, self-assembling and binding the first ends of the second set of carbon nanotubes to the core, functionalizing second ends of the second set of the carbon nanotubes with targeting molecules for specific targeted cells, and co-functionalizing first ends of a third set of carbon nanotubes with the second complementary affinity agent, self-assembling and binding the first ends of the third set of carbon nanotubes to the core, loading the third set of carbon nanotubes with treatment molecules for the specific targeted cells to which the targeting molecules attach for transferring the treatment molecules from the third set of carbon nanotubes to the specific targeted cells.

21. The process of claim 20, wherein the functionalizing and co-functionalizing plural nanomaterials comprise functionalizing and co-functionalizing plural carbon nanotubes.

22. The process of claim 21, wherein the functionalizing comprises functionalizing a first set of the carbon nanotubes with a first affinity agent, and a functionalizing second set of the carbon nanotubes with a second complementary affinity agent having an affinity for the first agent.

23. The process of claim 22, wherein the functionalizing with the first affinity agent and the second complementary affinity agent further comprise functionalizing the carbon nanotubes with biological molecules.

24. The process of claim 22, wherein the functionalizing with the first and second affinity agents comprises with respectively functionalizing the first and second sets of carbon nanotubes with streptavidin and biotin for self assembling the plural nanotubes into plural virus-like assemblies.

25. The process of claim 24, wherein the biotin-functionalized carbon nanotubes of the second set are co-functionalized with the specific cell targeting material.

26. The process of claim 25, wherein the first set of streptavidin co-functionalized carbon nanotubes is co-functionalized with the payload cell treatment molecules for the specific cells.

27. The process of claim 26, further comprising attaching plural biotin co-functionalized carbon nanotubes of the second set to each streptavidin co-functionalized carbon nanotube of the first set.

28. The process of claim 23, wherein the first set of co-functionalized carbon nanotubes is co-functionalized with the payload cell treatment molecules for the specific cells.

29. The process of claim 28, wherein the second set of carbon nanotubes is co-fuctionalized with the cell targeting molecules.

30. The process of claim 29, wherein the first and second affinity agents self assemble the plural nanotubes into plural virus-like assemblies.

31. The process of claim 20, wherein the materials co-functionalized with the specific cell targeting molecules have combinations of cell targeting molecules.

32. The process of claim 20, further comprising irradiating the nanomaterials with near infrared energy in vivo through tissue and heating the nanomaterials to release or activate the cell treatment payload or to rupture the targeted specific cells.

\* \* \* \* \*